(12) United States Patent
Horiguchi

(10) Patent No.: US 6,500,002 B2
(45) Date of Patent: Dec. 31, 2002

(54) ORAL CAVITY SPREADING APPARATUS

(75) Inventor: Shoji Horiguchi, Tokyo (JP)

(73) Assignees: Sintobrator, Ltd., Aichi-ken (JP); D & D Corporation, Tokyo (JP); Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/900,197

(22) Filed: Jul. 9, 2001

(65) Prior Publication Data

US 2002/0022211 A1 Feb. 21, 2002

(30) Foreign Application Priority Data

Jul. 12, 2000 (JP) .......................... 2000-211557

(51) Int. Cl.$^7$ ................................................ A61C 5/00
(52) U.S. Cl. ..................................................... 433/140
(58) Field of Search .......................... 433/140; 600/238; 128/862

(56) References Cited

U.S. PATENT DOCUMENTS 5,199,872 A * 4/1993 Leal ............................ 433/136
5,347,996 A * 9/1994 Huan .......................... 433/140

FOREIGN PATENT DOCUMENTS

JP 56-33524 8/1981

* cited by examiner

Primary Examiner—John J. Wilson
(74) Attorney, Agent, or Firm—Bacon & Thomas, PLLC

(57) ABSTRACT

An oral cavity spreading apparatus. The apparatus includes a pair of mouth corner hooks capable of being inserted into the oral cavity to spread the corners of the mouth, wing portions protruding individually outward from the mouth corner hooks and capable of spreading the inner part of the oral cavity, and a substantially U-shaped spring arm portion connecting the mouth corner hooks. The mouth corner hooks are adapted to be pressed toward each other against the urging force of the spring arm portion so that the respective end portions of the mouth corner hooks engage each other and the wing portions are steadily rotated inward and toward each other around the point of engagement between the end portions as a pivot as the mouth corner hooks are inserted into the oral cavity.

7 Claims, 5 Drawing Sheets

ORAL CAVITY SPREADING APPARATUS

CROSS-REFERENCE TO RELATED APPLICATIONS

This application is based upon and claims the benefit of priority from the prior Japanese Patent Application No. 2000-211557, filed Jul. 12, 2000, the entire contents of which are incorporated herein by reference.

BACKGROUND OF THE INVENTION

1. Field of the Invention

The present invention relates to an oral cavity spreading apparatus adapted to be used in, for example, medical examination, medical care, photographing, etc. for the interior of the oral cavity or the pharyngeal region, or oral muscle function training, or in inserting a cannula or gastrocamera into the trachea.

2. Description of the Related Art

An oral cavity spreading apparatus of this type is described in Jpn. UM Appln. KOKOKU Publication No. 56-33524, for example.

The apparatus described in Jpn. UM Appln. KOKOKU Publication No. 56-33524 comprises a pair of mouth corner hooks, left and right, which are connected to each other by means of a substantially U-shaped spring arm.

In operating this oral cavity spreading apparatus, a user first holds the left- and right-hand mouth corner hooks with his/her hand, and presses the hooks inward against the urging force of the spring arm. Thereupon, the crosswise dimension between the mouth corner hooks is reduced. Then, the narrowed mouth corner hooks are inserted into the oral cavity of a patient and hooked on the opposite corners of the mouth. Thereafter, the hand is released from the mouth corner hooks. Thereupon, the mouth corner hooks are moved away from each other to spread the mouth corners left and right by means of the restoring force of the spring arm. Thus, the interior of the oral cavity can be subjected to medical examination, medical care, photographing, etc.

Although the mouth corner hooks can be conveniently used in carrying out medical examination, medical care, photographing, etc. for the anterior tooth portions, they cannot spread alone the inner part of the oral cavity. Thus, the mouth corner hooks cannot be used for the posterior tooth portions without any problem.

Accordingly, there has recently been developed an oral cavity spreading apparatus that is provided with wing portions protruding individually outward from the respective outside portions of left- and right-hand mouth corner hooks. These wing portions serve to spread the inner part of the oral cavity, thereby widening the field of vision that leads to the posterior tooth portions.

If the wing portions are formed protruding outward from the mouth corner hooks, individually, however, the crosswise dimension between them increases, so that the wing portions hinder the apparatus from being easily inserted into the oral cavity, although they can widen the field of vision to the posterior tooth portions. Thus, the oral cavity spreading apparatus inflicts pain on the patient, and its usability for users is not satisfactory.

BRIEF SUMMARY OF THE INVENTION

The present invention has been contrived in consideration of these circumstances, and its object is to provide an oral cavity spreading apparatus, which can be easily inserted into the oral cavity even though it is provided with wing portions that project outward or toward the corners of the mouth.

An oral cavity spreading apparatus according to the present invention comprises a pair of mouth corner hooks capable of being inserted into the oral cavity to spread the corners of the mouth, wing portions protruding individually outward from the mouth corner hooks and capable of spreading the inner part of the oral cavity, and a substantially U-shaped spring arm portion connecting the mouth corner hooks, the mouth corner hooks being adapted to be pressed toward each other against the urging force of the spring arm portion so that the respective end portions of the mouth corner hooks engage each other and the wing portions are steadily rotated inward and toward each other around the point of engagement between the end portions as a pivot as the mouth corner hooks are inserted into the oral cavity.

As the apparatus constructed in this manner is inserted into the oral cavity, the wing portions on the paired mouth corner hooks can be steadily kept in parallel relation, so that the crosswise dimension between them can be reduced considerably. Thus, the apparatus can be easily inserted into the oral cavity.

Further, the structure of the pivot is made small enough not to hinder the apparatus from being fitted into the oral cavity.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently embodiments of the invention, and together with the general description given above and the detailed description of the embodiments given below, serve to explain the principles of the invention.

DETAILED DESCRIPTION OF THE INVENTION

Preferred embodiment of the present invention will now be described in detail with reference to the accompanying drawings.

Figure 1:
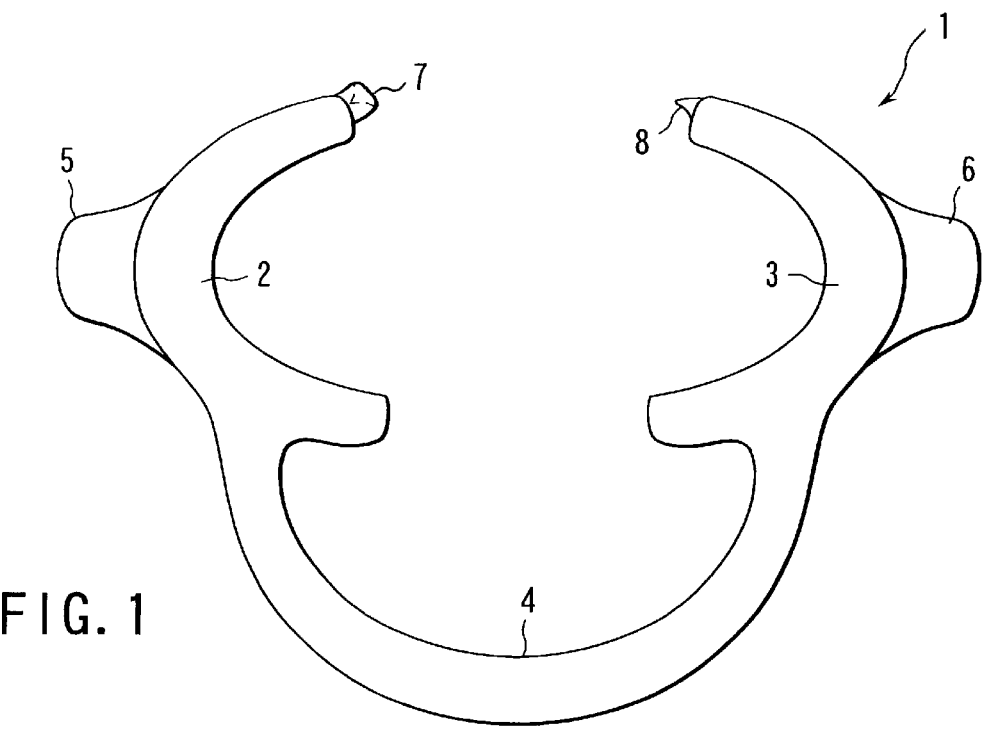
FIG. 1 is a front view of an oral cavity spreading apparatus according to a first embodiment of the present invention.
Figure 2:
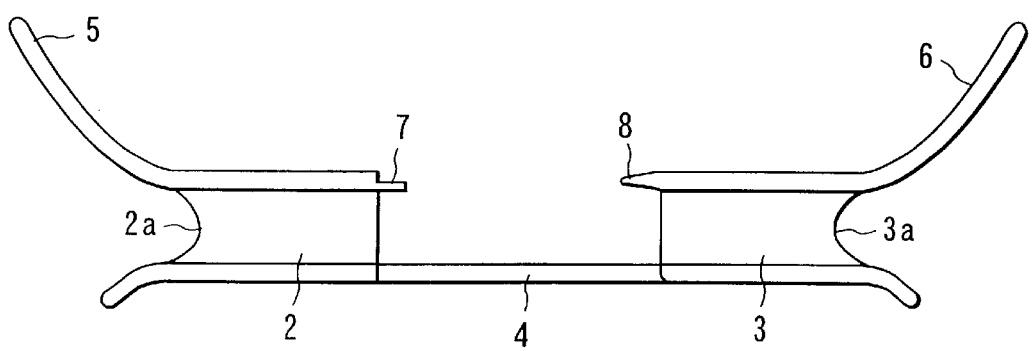
FIG. 2 is a top view of the oral cavity spreading apparatus.

FIGS. 1 and 2 are a front view and a top view, respectively, of an oral cavity spreading apparatus 1 according to a first embodiment of the present invention.

The oral cavity spreading apparatus 1 comprises a pair of mouth corner hooks 2 and 3, left and right, which are arcuate as viewed frontally, and a substantially U-shaped spring arm portion 4 that connects the respective lower parts of the hooks 2 and 3.

The left- and right-hand mouth corner hooks 2 and 3 are opposed to each other with a given space between them. Grooves 2a and 3a are formed on the respective outer peripheral side portions of the hooks 2 and 3, respectively. Wing portions 5 and 6 are formed integrally on the rear side of the corner hooks 2 and 3, respectively, so as to extend horizontally outward.

The grooves 2a and 3a of the mouth corner hooks 2 and 3 serve to receive the opposite corners of the mouth, and the wing portions 5 and 6 to spread the inner part of the oral cavity.

The mouth corner hooks 2 and 3 and the substantially U-shaped spring arm portion 4 is molded integrally from a highly elastic synthetic resin material, such as plastics, polycarbonate, polyethylene, polypropylene, etc.

Figure 3:
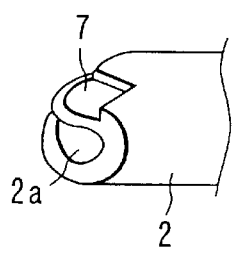
FIG. 3 is a perspective view showing a recess formed in the end portion of a left-hand mouth corner hook.
Figure 4:
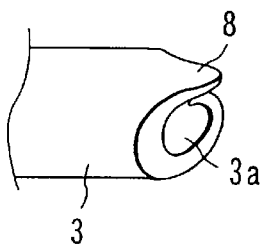
FIG. 4 is a perspective view showing a projection formed protruding from the end portion of a right-hand mouth corner hook.

A recess 7 is formed in the upper end portion of the left-hand mouth corner hook 2, as is also shown in FIG. 3, while a projection protrudes integrally from the upper end portion of the right-hand mouth corner hook 3, as is also shown in FIG. 4.

When the left- and right-hand mouth corner hooks 2 and 3 are pressed inward so as to approach each other in the manner mentioned later, the projection 8 of the right-hand corner hook 3 is detachably fitted into the recess 7 of the left-hand corner hook 2.

The use of the oral cavity spreading apparatus 1 will now be described with reference to FIGS. 5 to 8.

Figure 5:
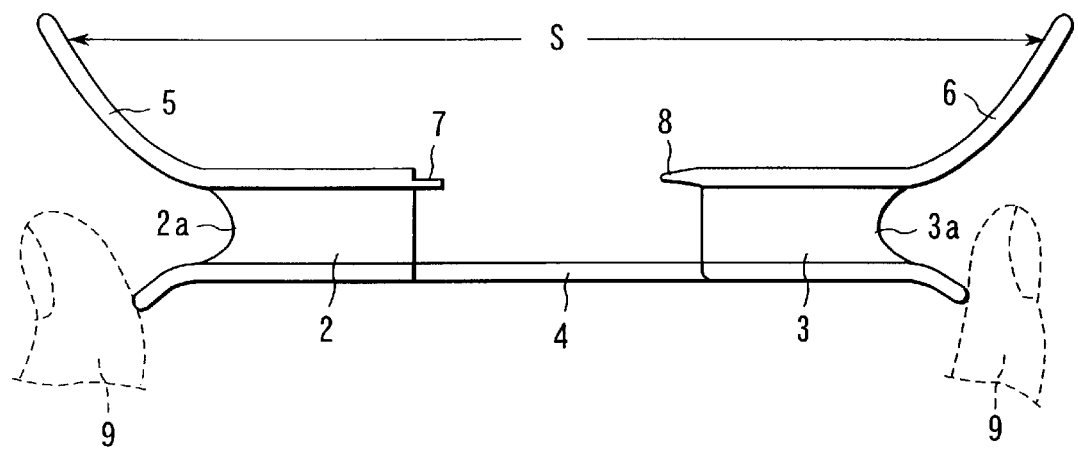
FIG. 5 is a view showing the way the left- and right-hand mouth corner hooks are held with fingers as the apparatus is inserted into the oral cavity.
Figure 6:
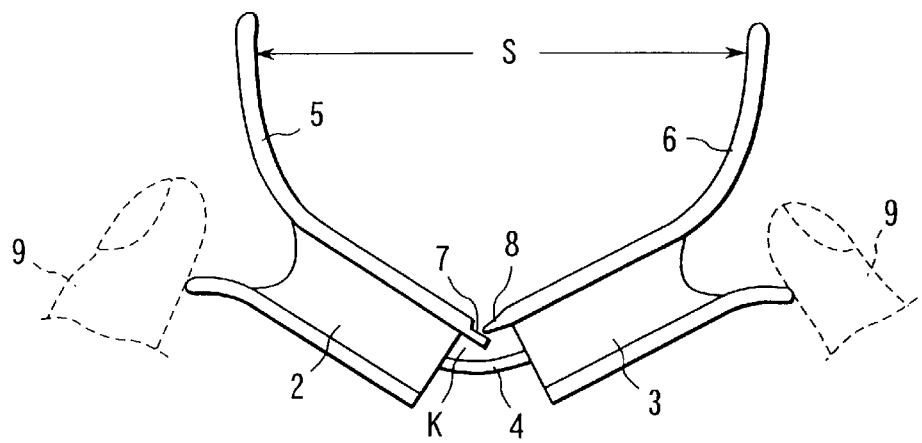
FIG. 6 is a view showing the way the mouth corner hooks are pressed inward so that the recess and the projection engage each other.

First, a user holds the respective outer peripheral portions of the left- and right-hand mouth corner hooks 2 and 3 with fingers 9 of his/her hand, as shown in FIG. 5, and presses the hooks 2 and 3 inward against the urging force of the spring arm portion 4. Thereupon, the corner hooks 2 and 3 are pushed in for a given distance, and the projection 8 of the right-hand corner hook 3 is inserted into and engages the recess 7 of the left-hand corner hook 2, as shown in FIG. 6.

Figure 7:
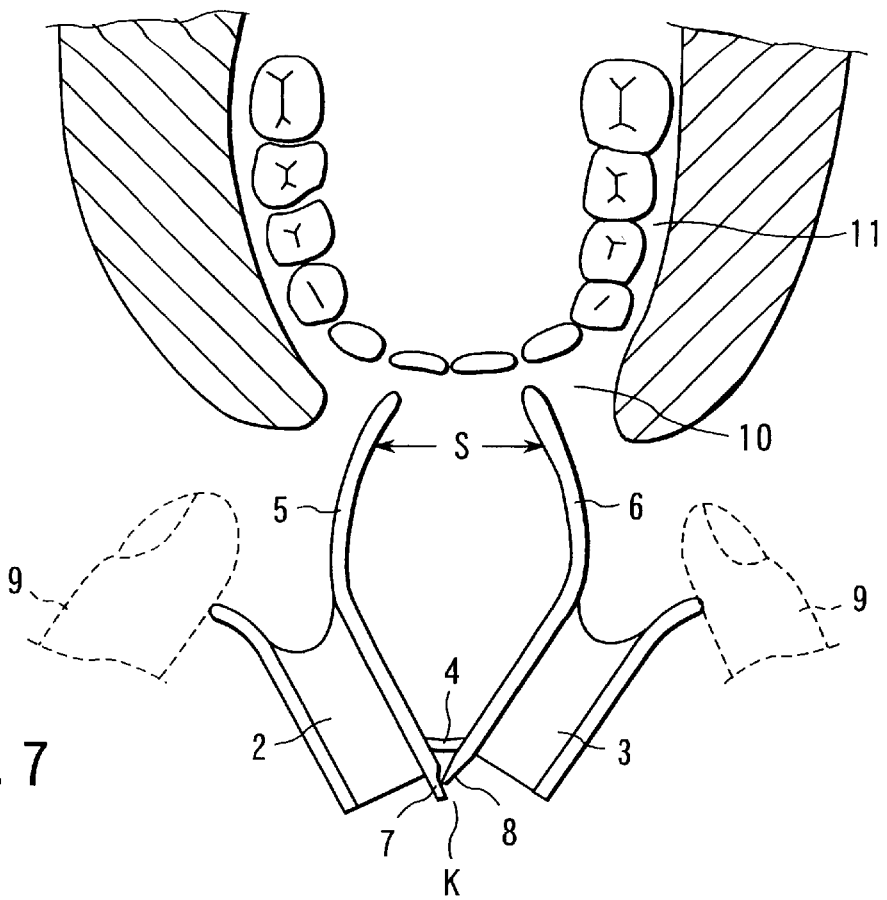
FIG. 7 is a view showing the way wing portions on the mouth corner hooks are rotated inward and toward each other around the point of engagement of the recess and the projection as a pivot.
Figure 8:
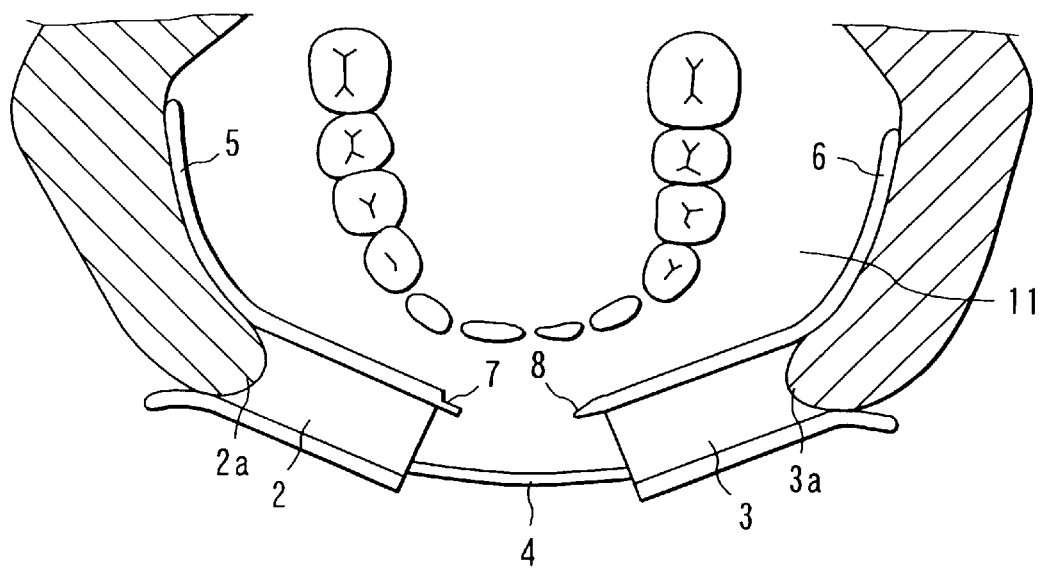
FIG. 8 is a view showing the way the interior of the oral cavity is spread by means of the mouth corner hooks inserted therein.

If the left- and right-hand mouth corner hooks 2 and 3 in this state are further pressed inward, they rotate inward around the point of engagement between the recess 7 and the projection 8 as a pivot K, as shown in FIG. 7. Thereupon, the wing portions 5 and 6 of the corner hooks 2 and 3 rotate inward and toward each other so that they become substantially parallel to each other. Thus, a crosswise dimension S between the wing portions 5 and 6 is reduced.

After the crosswise dimension S between the wing portions 5 and 6 is reduced in this manner, the wing portions 5 and 6 are inserted into a patient's oral cavity 11 through mouth corners 10, and the opposite mouth corners 10 are fitted individually into the grooves 2a and 3a on the respective outer peripheral portions of the left- and right-hand mouth corner hooks 2 and 3. Thereafter, the fingers 9 are released from the outside of the corner hooks 2 and 3. Thereupon, the spring arm portion 4 is restored in its spreading direction, and the corner hooks 2 and 3 move away from each other. As this is done, the patient's mouth corners 10 are spread left and right, and the inner part of the oral cavity 11 is also spread at the same time by means of the wing portions 5 and 6.

After the mouth corners 10 and the inner part of the oral cavity 11 are spread in this manner, the anterior and posterior tooth portions in the oral cavity 11 are subjected to medical examination, medical care, photographing, etc.

As mentioned before, the recess 7 and the projection 8 are formed in or on the left- and right-hand mouth corner hooks 2 and 3. After the corner hooks 2 and 3 are pressed inward so that the recess 7 and the projection 8 engage each other, the wing portions 5 and 6 of the corner hooks 2 and 3 are steadily rotated inward and toward each other around the point of engagement between the recess 7 and the projection 8 as the pivot K. Accordingly, the wing portions 5 and 6 can be steadily kept in parallel relation, so that the crosswise dimension S between them can be reduced considerably.

Thus, the wing portions 5 and 6 of the left- and right-hand mouth corner hooks 2 and 3 can be easily inserted into the patient's oral cavity 11, so that the patient can be eased considerably of suffering, and the usability of the apparatus can be improved.

Since the pivot K has so small a structure that it never hinder the apparatus from being fitted into the oral cavity 11.

Figure 9:
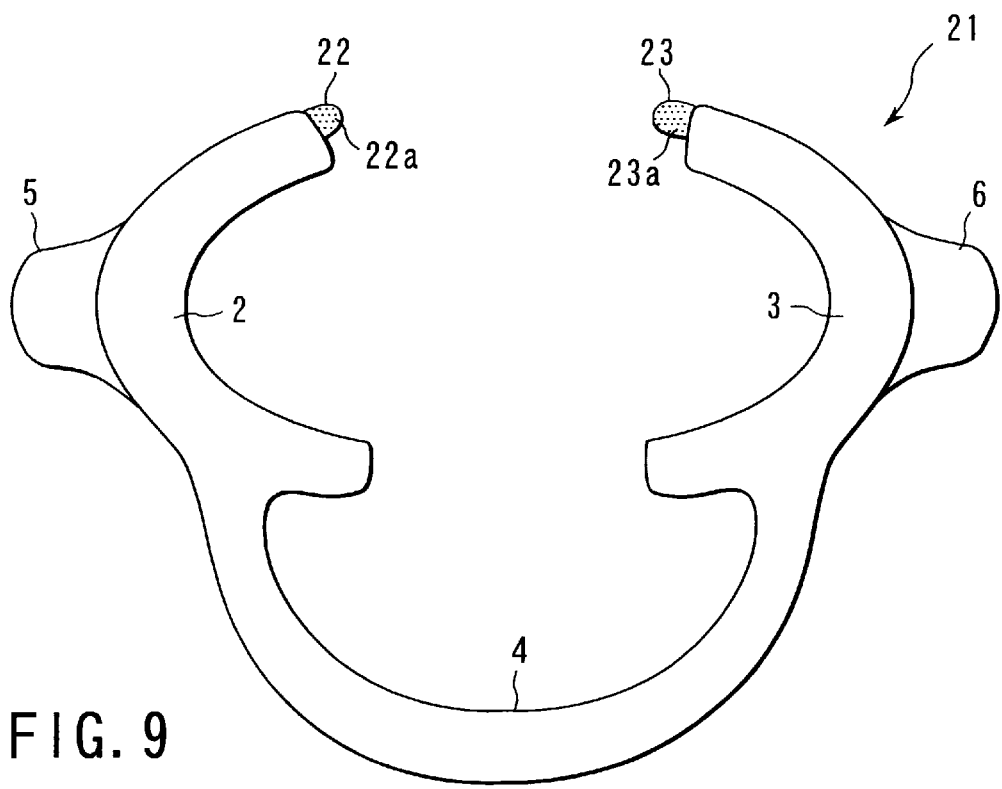
FIG. 9 is a front view of an oral cavity spreading apparatus according to a second embodiment of the invention.
Figure 10:
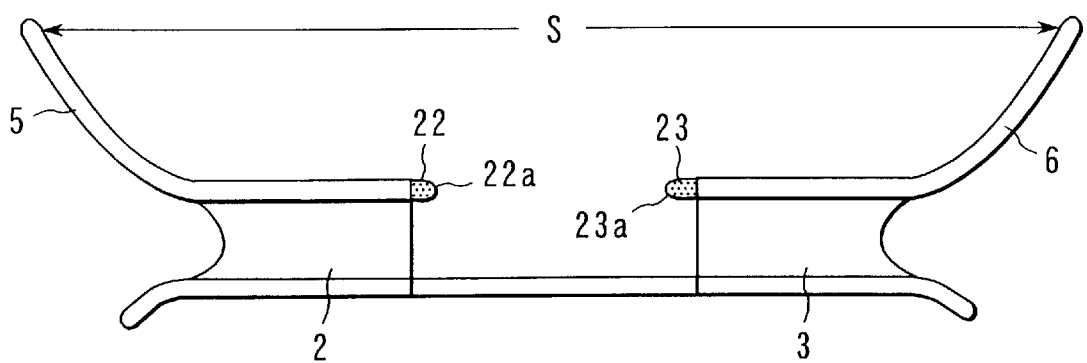
FIG. 10 is a top view of the oral cavity spreading apparatus shown in FIG. 9.

FIGS. 9 and 10 are a front view and a top view, respectively, of an oral cavity spreading apparatus 21 according to a second embodiment of the invention.

In the description to follow, like reference numerals are used to designate like portions of the first and second embodiments, and a description of those portions is omitted.

In the second embodiment, projections 22 and 23 are molded protruding from the respective end portions of left- and right-hand mouth corner hooks 2 and 3, respectively. The projections 22 and 23 are formed of a highly viscous material with high frictional resistance, such as natural rubber, synthetic rubber, or ethylene-vinyl acetate copolymer, and their surfaces form adhesive surfaces 22a and 23a, respectively.

Figure 11:
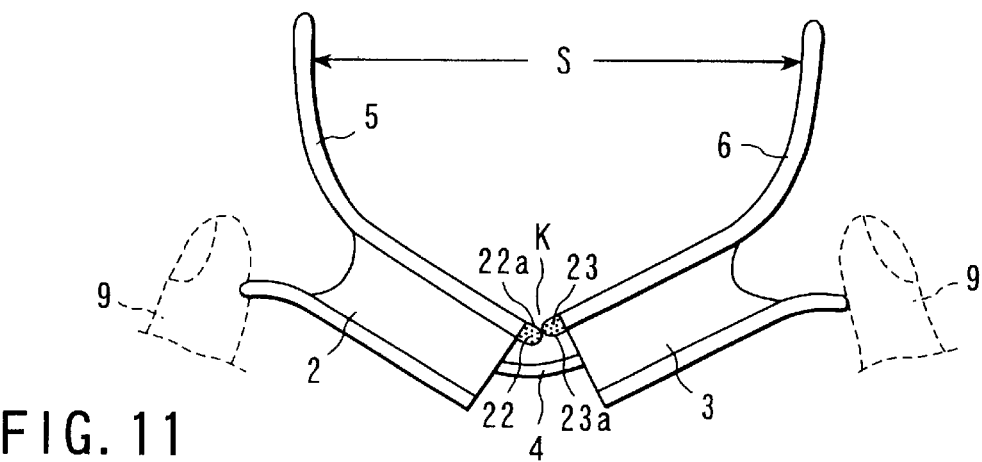
FIG. 11 is a view showing the way left- and right-hand mouth corner hooks are pressed inward so that their respective end portions abut against each other as the apparatus is inserted into the oral cavity.
Figure 12:
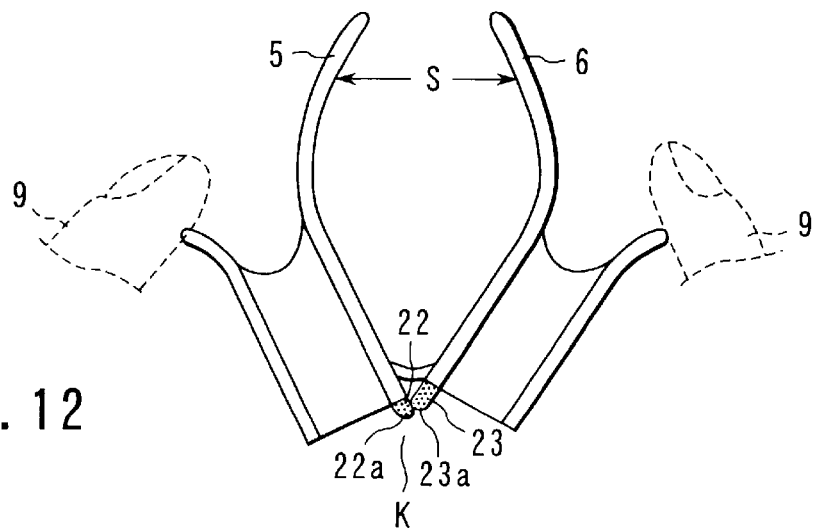
FIG. 12 is a view showing the way wing portions on the mouth corner hooks are rotated inward and toward each other around the abutting end portions of the corner hooks as a pivot.

In inserting the left- and right-hand mouth corner hooks 2 and 3 into the oral cavity 11, the user holds the respective outer peripheral portions of the corner hooks 2 and 3 with the fingers 9, as shown in FIG. 11, and presses the hooks 2 and 3 inward against the urging force of a spring arm portion 4. Thereupon, the corner hooks 2 and 3 are pushed in for a given distance, and the adhesive surfaces 22a and 23a of the projections 22 and 23 on the respective end portions of the corner hooks 2 and 3 come into contact with each other. If the left- and right-hand corner hooks 2 and 3 in this state are further pressed inward, they rotate inward around their abutting projections 22 and 23 as a pivot K, as shown in FIG. 12. Thereupon, wing portions 5 and 6 of the corner hooks 2 and 3 rotate inward and toward each other so that they become substantially parallel to each other. Thus, a crosswise dimension S between the wing portions 5 and 6 is reduced.

In this second embodiment, as in the foregoing first embodiment, the wing portions 5 and 6 of the left- and right-hand mouth corner hooks 2 and 3 can be easily inserted into the patient's oral cavity 11, so that the patient can be eased considerably of suffering, and the usability of the apparatus can be improved.

In the second embodiment, moreover, the projections 22 and 23 on the respective end portions of the left- and right-hand mouth corner hooks 2 and 3 are formed of the material with high frictional resistance. Alternatively, however, only one of the projections of the corner hooks 2 and 3 may be formed of a high-friction material.

In the second embodiment, furthermore, the projections 22 and 23 on the respective end portions of the left- and right-hand mouth corner hooks 2 and 3, which are formed of the material with high frictional resistance, have the adhesive surfaces 22a and 23a. Alternatively, however, the frictional resistance may be increased by roughening the respective surfaces of the respective surfaces of the end projections 22 and 23 of the corner hooks 2 and 3.

The surface of the projection on the end portion of only one of the mouth corner hooks 2 and 3 may be roughened without roughening the surfaces of both the projections 22 and 23 on the respective end portions of the corner hooks 2 and 3.

Figure 13:
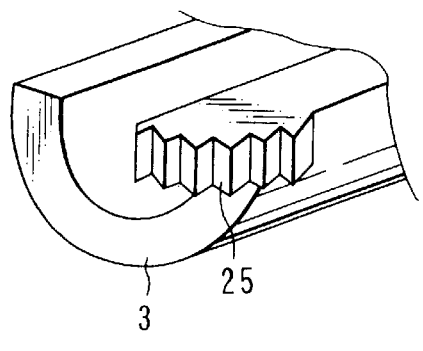
FIG. 13 is a perspective view showing a gear-shaped groove portion on the end portion of a left-hand mouth corner hook according to a third embodiment of the invention.
Figure 14:
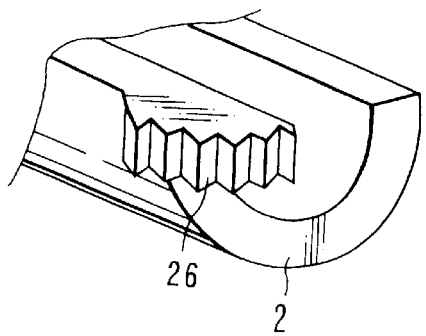
FIG. 14 is a perspective view showing a gear-shaped groove portion on the end portion of a right-hand mouth corner hook.

FIGS. 13 and 14 show a third embodiment of the invention.

In this third embodiment, dentate portions 25 and 26 in the form of a continuous gear each are formed on the respective end portions of left- and right-hand mouth corner hooks 2 and 3, respectively. The dentilated portions 25 and 26 are caused to engage each other so that the point of their engagement serves as a pivot K around which wing portions 5 and 6 of the corner hooks 2 and 3 rotate.

Further, each of the dentate portions on the respective end portions of the left- and right-hand mouth corner hooks 2 and 3 may be a simple structure in place of a continuous gear-shaped structure, and may have a straight, dog-legged, or zigzag shape.

It is to be understood that the present invention is not limited to the embodiments described above, and that various changes and modifications may be effected therein by one skilled in the art without departing from the scope or spirit of the invention.

In inserting the paired mouth corner hooks into the oral cavity, according to the present invention, as described herein, the corner hooks are pressed toward each other against the urging force of the spring arm portion so that their respective end portions engage each other, and the wing portions are steadily rotated inward and toward each other around the point of engagement between the end portions as the pivot. Accordingly, the wing portions of the corner hooks can be steadily kept in parallel relation, so that the crosswise dimension between them can be reduced considerably.

Thus, the apparatus can be easily inserted into the patient's oral cavity without inflicting pain on the patient, and its usability can be improved.

Since the pivot has a small structure, moreover, it never hinders the apparatus from being fitted into the oral cavity.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An oral cavity spreading apparatus comprising:
    a pair of mouth corner hooks capable of being inserted into the oral cavity to spread the corners of the mouth;
    wing portions protruding individually outward from the mouth corner hooks and capable of spreading the inner part of the oral cavity; and
    a substantially U-shaped spring arm portion connecting the mouth corner hooks,
    the mouth corner hooks being adapted to be pressed toward each other against the urging force of the spring arm portion so that the respective end portions of the mouth corner hooks engage each other and the wing portions are steadily rotated inward and toward each other around the point of engagement between the end portions as a pivot as the mouth corner hooks are inserted into the oral cavity.

2. An oral cavity spreading apparatus according to claim 1, wherein said mouth corner hooks, wing portions, and spring arm portion are molded integrally from an elastic synthetic resin material.

3. An oral cavity spreading apparatus comprising:
    a pair of mouth corner hooks capable of being inserted into the oral cavity to spread the corners of the mouth;
    wing portions protruding individually outward from the mouth corner hooks and capable of spreading the inner part of the oral cavity; and
    a substantially U-shaped spring arm portion connecting the mouth corner hooks,
    the mouth corner hooks being adapted to be pressed toward each other against the urging force of the spring arm portion so that the respective end portions of the mouth corner hooks engage each other and the wing portions are steadily rotated inward and toward each other around the point of engagement between the end portions as a pivot as the mouth corner hooks are inserted into the oral cavity,
    one the mouth corner hooks being formed having a recess in the end portion thereof and the other having a projection on the end portion thereof such that the point of engagement between the recess and the projection forms the pivot.

4. An oral cavity spreading apparatus according to claim 3, wherein said recess and said projection are a single recess or projection each or a plurality of continuous recesses or projections each.

5. An oral cavity spreading apparatus comprising:
    a pair of mouth corner hooks capable of being inserted into the oral cavity to spread the corners of the mouth;
    wing portions protruding individually outward from the mouth corner hooks and capable of spreading the inner part of the oral cavity; and
    a substantially U-shaped spring arm portion connecting the mouth corner hooks,
    the mouth corner hooks being adapted to be pressed toward each other against the urging force of the spring arm portion so that the respective end portions of the mouth corner hooks engage each other and the wing portions are steadily rotated inward and toward each other around the point of engagement between the end portions as a pivot as the mouth corner hooks are inserted into the oral cavity, the surface of the end portion of at least one of the mouth corner hooks having high frictional resistance so that the point of engagement between the respective end portions of the mouth corner hooks forms the pivot.

6. An oral cavity spreading apparatus according to claim 5, wherein at least one of the surfaces of the end portions of said mouth corner hooks are adhesive surfaces.

7. An oral cavity spreading apparatus according to claim 5, wherein at least one of the surfaces of the end portions of said mouth corner hooks are rough surfaces.

* * * * *